US012582169B2

(12) United States Patent
Lei et al.

(10) Patent No.: US 12,582,169 B2
(45) Date of Patent: Mar. 24, 2026

(54) ELECTRONIC VAPORIZATION DEVICE AND VAPORIZER THEREOF

(71) Applicant: SHENZHEN SMOORE TECHNOLOGY LIMITED, Shenzhen (CN)

(72) Inventors: Guilin Lei, Shenzhen (CN); Dan Xu, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 391 days.

(21) Appl. No.: 18/335,438

(22) Filed: Jun. 15, 2023

(65) Prior Publication Data

US 2023/0320426 A1      Oct. 12, 2023

Related U.S. Application Data

(63) Continuation of application No. PCT/CN2020/138967, filed on Dec. 24, 2020.

(51) Int. Cl.
| | |
|---|---|
| *A24F 40/48* | (2020.01) |
| *A24F 40/10* | (2020.01) |
| *A61M 15/06* | (2006.01) |

(52) U.S. Cl.
CPC .............. *A24F 40/48* (2020.01); *A24F 40/10* (2020.01); *A61M 15/06* (2013.01)

(58) Field of Classification Search
None
See application file for complete search history.

(56) References Cited

U.S. PATENT DOCUMENTS

| | | | |
|---|---|---|---|
| 2011/0094523 A1* | 4/2011 | Thorens | ................... A24F 40/44 |
| | | | 131/194 |
| 2017/0086506 A1* | 3/2017 | Rado | ...................... A24F 40/485 |
| 2018/0000160 A1* | 1/2018 | Taschner | ................. A24F 40/46 |

(Continued)

FOREIGN PATENT DOCUMENTS

| | | |
|---|---|---|
| CN | 204070562 U | 1/2015 |
| CN | 204146318 U | 2/2015 |
| CN | 110602957 A | 12/2019 |

(Continued)

OTHER PUBLICATIONS

Patent Cooperation Treaty, International Search Report and Written Opinion, International Application No. PCT/CN2020/138967 (Sep. 6, 2021).

(Continued)

*Primary Examiner* — Cynthia Szewczyk
(74) *Attorney, Agent, or Firm* — Leydig, Voit & Mayer, Ltd.

(57) ABSTRACT

A vaporizer includes: a housing; and a vaporization assembly arranged in the housing; a vaporization cavity for accommodating the vaporization assembly being arranged in the housing, and an airflow channel arranged in the housing at one side of the vaporization cavity and in communication with the vaporization cavity; an air inlet in communication with the vaporization cavity; and an airflow guide structure arranged in the vaporization cavity for guiding an airflow at the air inlet. The airflow guide structure is arranged close to the airflow channel.

12 Claims, 6 Drawing Sheets

(56)  References Cited

U.S. PATENT DOCUMENTS

2020/0128875  A1*    4/2020   Cane ...................... A24F 40/46

FOREIGN PATENT DOCUMENTS

| CN | 210054649 | U  | 2/2020 |
|----|-----------|----|--------|
| CN | 211211432 | U  | 8/2020 |
| CN | 211353913 | U  | 8/2020 |
| CN | 211910517 | U  | 11/2020 |
| WO | 2011050943 | A1 | 5/2011 |
| WO | 2011050943 | A8 | 5/2011 |
| WO | 2016082108 | A1 | 6/2016 |
| WO | 2018132955 | A1 | 7/2018 |

OTHER PUBLICATIONS

Chinese Patent Office, Office Action in Chinese Patent Application
No. 202011551367.4 (Jul. 30, 2024).
European Patent Office, Search Report in European Patent Application No. 20966460.6 (Oct. 9, 2023).

* cited by examiner

100

A

B

Existing electronic
vaporization device

Electronic vaporization device
of the present invention

Existing electronic
vaporization device

Electronic vaporization device
of the present invention

Existing electronic
vaporization device

Electronic vaporization device
of the present invention

ELECTRONIC VAPORIZATION DEVICE AND VAPORIZER THEREOF

CROSS-REFERENCE TO PRIOR APPLICATION

This application is a continuation of International Patent Application No. PCT/CN2020/138967, filed on Dec. 24, 2020. The entire disclosure is hereby incorporated by reference herein.

FIELD

The present invention relates to a vaporization device, and more specifically, to an electronic vaporization device and a vaporizer thereof.

BACKGROUND

In the interior of electronic vaporization devices with a side airway in the related art, accumulation of a large amount of high-temperature vapor is easily formed at a closed end.

In the interior of electronic vaporization device with a side airway in the related art, a large amount of high-temperature vapor accumulation is easily formed at a closed end, which leads to two problems: One is that the vapor condenses to form condensate, and the other is that a high-temperature region is formed at the closed end, forming plastic melting, which increases a risk of miscellaneous gas and scorched smell of the vapor.

SUMMARY

In an embodiment, the present invention provides a vaporizer, comprising: a housing; and a vaporization assembly arranged in the housing, a vaporization cavity configured to accommodate the vaporization assembly being arranged in the housing, and an airflow channel being arranged in the housing at one side of the vaporization cavity and in communication with the vaporization cavity; an air inlet in communication with the vaporization cavity; and an airflow guide structure arranged in the vaporization cavity and configured to guide an airflow at the air inlet, wherein the airflow guide structure is arranged close to the airflow channel.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
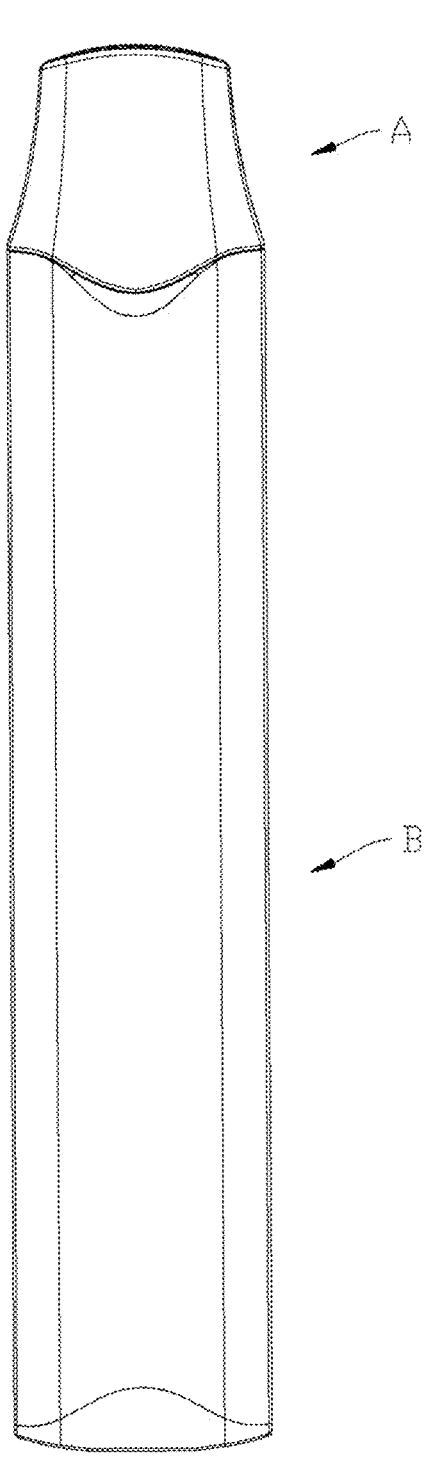
FIG. 1 is a schematic structural diagram of an electronic vaporization device according to some embodiments of the present invention.

In an embodiment, the present invention provides an improved vaporizer and further provide an improved electronic vaporization device.

In an embodiment, the present invention provides a vaporizer, including a housing and a vaporization assembly arranged in the housing, where a vaporization cavity for accommodating the vaporization assembly is arranged in the housing, an airflow channel is further arranged in the housing, and the airflow channel is arranged at one side of the vaporization cavity and in communication with the vaporization cavity; and the vaporizer further includes an air inlet in communication with the vaporization cavity, and an airflow guide structure arranged in the vaporization cavity to guide an airflow at the air inlet, where the airflow guide structure is arranged close to the airflow channel.

Preferably, the airflow guide structure includes an airflow guide surface arranged opposite to the air inlet; and a set angle is formed between the airflow guide surface and an air inlet end surface of the air inlet.

Preferably, the set angle is an acute angle.

Preferably, the vaporization cavity further includes a closed region arranged opposite to the airflow channel;

the airflow guide surface is arranged towards the closed region to guide a part of the airflow to the closed region of the vaporization cavity, and squeeze, accelerate, and guide the airflow outputted to the airflow channel from the vaporization cavity.

Preferably, the air inlet includes a central axis; and the airflow guide structure is arranged at one side of the central axis.

Preferably, the size of the airflow guide structure is smaller than that of the vaporization cavity.

Preferably, the airflow guide structure is arranged between the vaporization assembly and the air inlet, and a spacing is reserved between the airflow guide structure and the vaporization assembly; and the spacing forms a communication channel that communicates the vaporization cavity with the airflow channel.

Preferably, the vaporization assembly includes a vaporization surface arranged opposite to the vaporization cavity;

the airflow guide structure further includes an overflow surface arranged opposite to the vaporization surface; and the communication channel is arranged between the overflow surface and the vaporization surface.

Preferably, the distance between the overflow surface and the vaporization surface is greater than zero and not greater than ⅔ of the height of the vaporization cavity.

Preferably, the cross section of the housing includes a length direction and a width direction; and two opposite sides of the airflow guide structure respectively extend to the side wall of the housing along the width direction of the housing.

Preferably, the airflow guide structure and the housing are integrally formed.

Preferably, the airflow guide structure is in the shape of a triangle, a wedge, or a trapezoid.

Preferably, the vaporizer further includes two electrode columns conductively connected to the vaporization assembly;

the two electrode columns are spaced apart; and the airflow guide structure is arranged between the two electrode columns.

Preferably, the vaporizer further comprises a base;

the housing is sleeved on the base; and the air inlet is arranged on the base.

The present invention further constructs an electronic vaporization device, including the vaporizer in the present invention and a power supply assembly connected to the vaporizer.

Beneficial Effects:

The electronic vaporization device and the vaporizer thereof of the present invention are implemented to achieve the following beneficial effects: By arranging the airflow guide structure, the vaporizer can guide the airflow from the air inlet to guide a part of the airflow to a closed end of a vaporization cavity, which can avoid accumulation of a large amount of high-temperature vapor at the closed end of the vaporization cavity, and avoid generation of condensate and a risk of miscellaneous gas and scorched smell of the vapor increased by plastic melting.

To provide a clearer understanding of the technical features, objectives, and effects of the present invention, specific implementations of the present invention are described in detail with reference to the accompanying drawings.

It should be understood that terms such as "upper" and "lower" are only for the convenience of describing the technical solutions of the present invention instead of indicating that the devices or elements need to have special differences, and therefore cannot be understood as a limitation on the present invention. It should be noted that when a member is considered to be "connected" to another member, the member may be directly connected to the another member or there may be an intermediate member between the two members. Unless otherwise defined, meanings of all technical and scientific terms used herein are the same as meanings generally understood by a person skilled in the technical field to which the present invention belongs. In this specification, terms used in this specification of the present invention are merely intended to describe objectives of the specific embodiments, but are not intended to limit the present invention.

FIG. 1 shows some preferred embodiments of an electronic vaporization device of the present invention. The electronic vaporization device 100 may be configured to vaporize a liquid medium such as cigarette liquid or medicine. In some embodiments, the electronic vaporization device 100 may include a vaporizer A and a power supply assembly B mechanically and electrically connected to the vaporizer A. The vaporizer A is configured to heat and vaporize the liquid medium, and the power supply assembly B is configured to supply power to the vaporizer. Preferably, the vaporizer A and the power supply assembly B are detachably connected.

Figure 2:
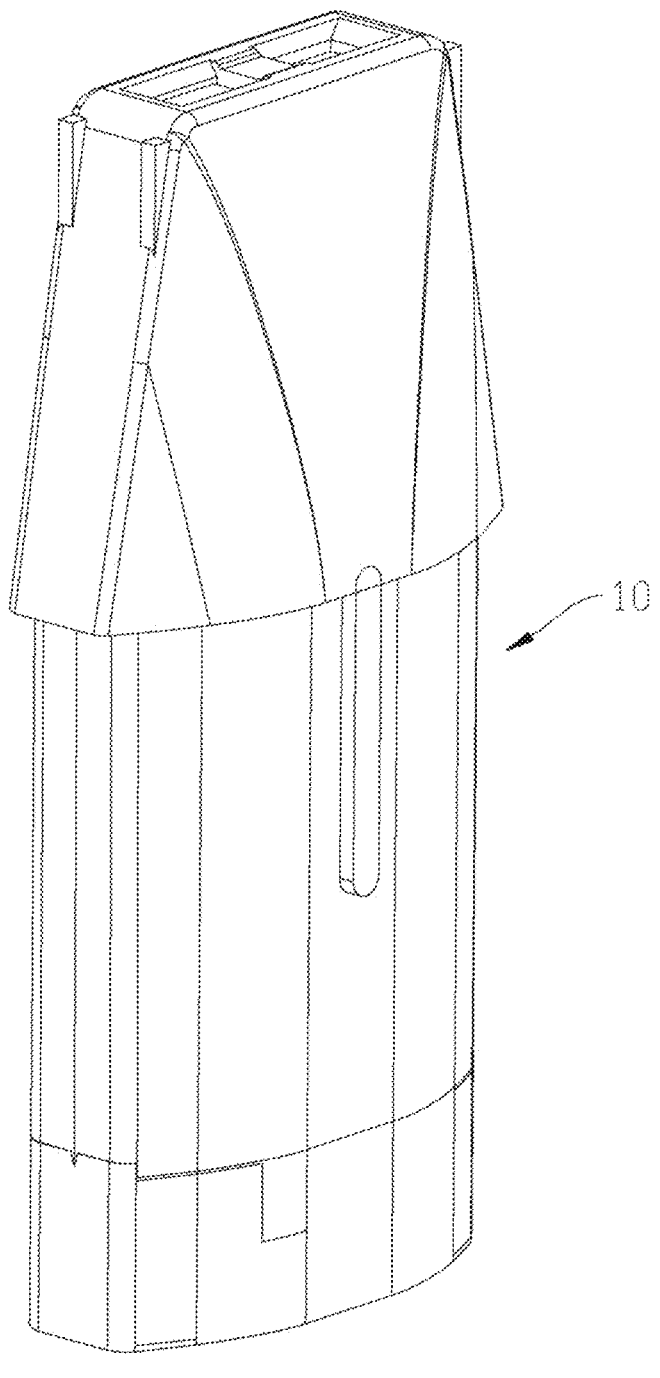
FIG. 2 is a schematic structural diagram of a vaporizer of the electronic vaporization device shown in FIG. 1.
Figure 3:
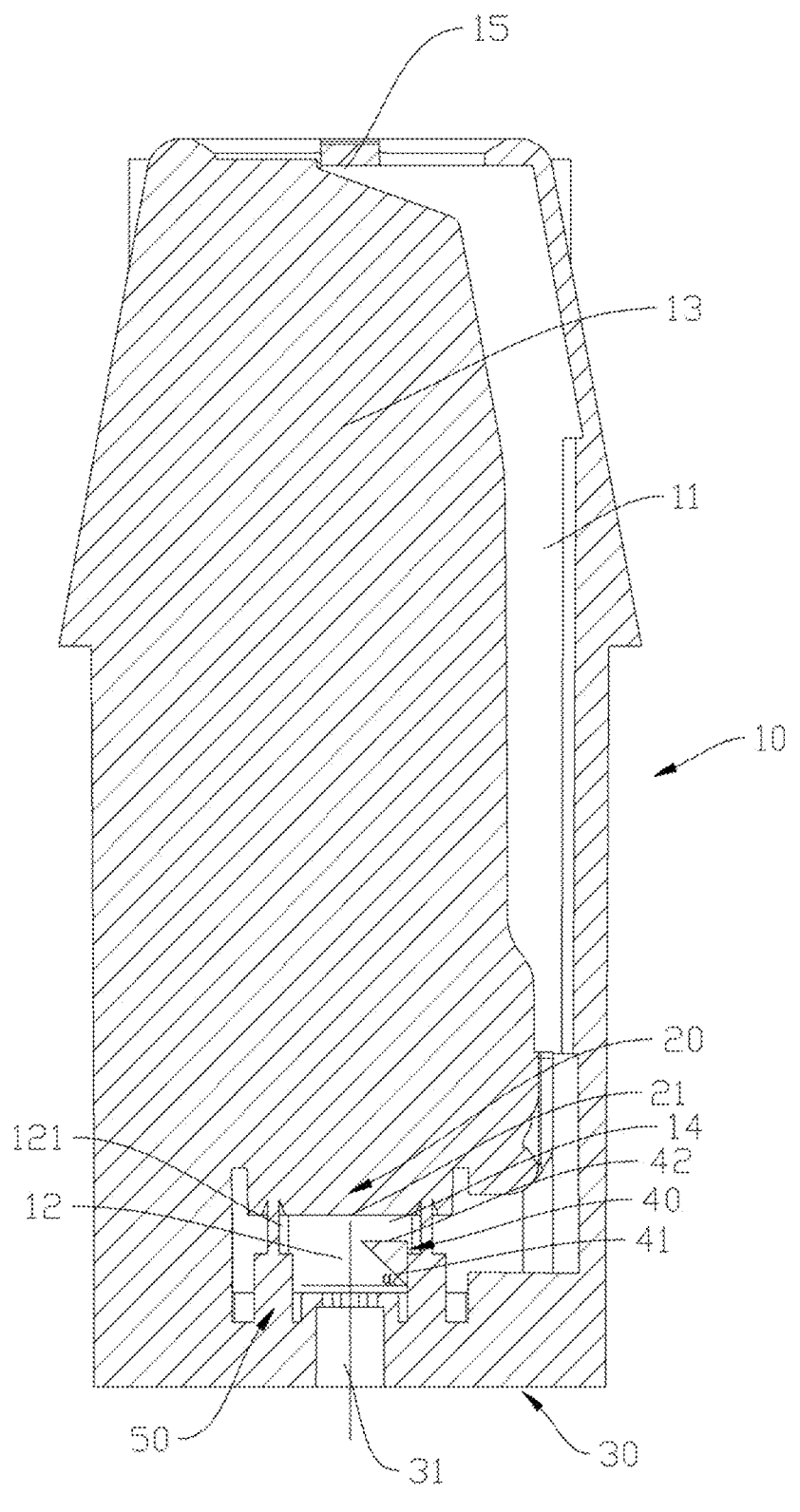
FIG. 3 is a cross-sectional view of the vaporizer shown in FIG. 2.

As shown in FIG. 2 and FIG. 3, in some embodiments, the vaporizer A includes a housing 10, a vaporization assembly 20, an airflow guide structure 40, and a base 30. The housing 10 is sleeved on the base 30 and may be configured to accommodate the vaporization assembly 20 and the airflow guide structure 40. The vaporization assembly 20 is arranged in the housing 10 and is configured to heat and vaporize the liquid medium. The airflow guide structure 40 is arranged in the housing 10 and may be configured to guide an airflow in the housing 10.

Further, in some embodiments, the housing 10 is in the shape of a cylinder, and the housing 10 is sleeved on the periphery of the vaporization assembly 20. The cross section of the housing 10 may be substantially rectangular, and the cross section of the housing 10 may include a length direction and a width direction. Certainly, it may be understood that, in some other embodiments, the cross section of the housing 10 may not be limited to a rectangle, and in some other embodiments, the cross section of the housing 10 may be elliptical, the length direction may be a long axis direction, and the width direction may be a short axis direction. A liquid storage cavity 13 may be formed inside the housing 10, the liquid storage cavity 13 is located at the upper part of the housing 10, and the liquid storage cavity 13 may be configured to accommodate the liquid medium. Specifically, in some embodiments, a vaporization cavity 12 is further arranged in the housing 10, and the vaporization assembly 20 may be accommodated in the vaporization cavity 12. The vaporization cavity 12 may be located at the lower part of the housing 10. In some embodiments, an airflow channel 11 is further arranged in the housing 10, and the airflow channel 11 is arranged at one side of the housing 10. Specifically, the airflow channel 11 may be located at one side of the vaporization cavity 12 and in communication with the vaporization cavity 12 to output vapor after vaporization. In some embodiments, the airflow channel 11 may extend along a longitudinal direction of the housing 10. In some embodiments, an air outlet 15 is provided on the housing 10. Specifically, the air outlet 15 may be provided at the top of the housing 10, and one end of the airflow channel 11 may be in communication with the air outlet 15 to convey vapor to the air outlet 15. In some embodiments, the vaporization cavity 12 further includes a closed region 121, and the closed region 121 is a region arranged opposite to the airflow channel 11.

Further, in some embodiments, the vaporization assembly 20 is arranged in the vaporization cavity 12, and the vaporization assembly 20 is in liquid guide connection to the liquid storage cavity 13 in the housing 10. In some embodiments, specifically, the housing 10 may further include an upper base body, the vaporization assembly 20 may be accommodated in the upper base body, the upper base body is provided with a liquid flowing hole in communication with the liquid storage cavity 13, and the liquid flowing hole is arranged opposite to the vaporization assembly 20 to convey liquid from the liquid storage cavity 13 to the vaporization assembly 20. In some embodiments, the vaporization assembly 20 includes a porous body and a heating body arranged on the porous body. The porous body may be a ceramic porous body. The heating body may be arranged on the porous body. In some embodiments, the heating body may be a heating sheet, and the heating sheet may be arranged on an end surface of the porous body opposite to the base 30. Specifically, the heating body may be pasted, printed or partially embedded on the end surface of the porous body opposite to the base 30. In some embodiments, the vaporization assembly 20 may include a vaporization surface 21. Specifically, the vaporization surface 21 may be arranged on the porous body, and the vaporization surface 21 may be an end surface of the porous body on which the heating body is arranged.

Further, in some embodiments, the base 30 may be located at an open end of the housing 10 to block the housing 10. In some embodiments, the base 30 and the housing 10 may be integrally formed. Certainly, it may be understood that, in some other embodiments, the base 30 and the housing 10 may not be limited to be integrally formed. In some embodiments, the vaporizer may further include an air inlet 31. Specifically, the air inlet 31 may be arranged on the base 30 and located at the middle part of the base 30. Specifically, the air inlet 31 may be arranged throughout the base 30 along a thickness direction of the base 30. The air inlet 31 may be in communication with the vaporization cavity 12, and may be used for an external airflow to enter the vaporization cavity 12, to further bring out the vapor in the vaporization cavity 12.

Further, in some embodiments, the airflow guide structure 40 may be arranged in the vaporization cavity 12 and in an air inlet direction of the air inlet 31, and arranged close to the airflow channel 11. In some embodiments, the airflow guide structure 12 may be located at one side of the central axis of the air inlet 31 and a protruding portion of the airflow guide structure is arranged not beyond the central axis to avoid blocking the central airflow. The airflow guide structure 12 may be configured to guide the airflow from the air inlet 31 to guide a part of the airflow to a closed end of the vaporization cavity 12, which can avoid accumulation of a large amount of high-temperature vapor at the closed end of the vaporization cavity 12, and avoid generation of condensate and a risk of miscellaneous gas and scorched smell of the vapor increased by plastic melting.

Further, in some embodiments, the airflow guide structure 40 may be in the shape of a triangle. Certainly, it may be understood that, in some other embodiments, the airflow guide structure 40 may not be limited to be in the shape of a triangle. In some other embodiments, the airflow guide structure 40 may be in a shape of a wedge or a trapezoid. In some embodiments, the size of the airflow guide structure 40 may be smaller than that of the vaporization cavity 12, thereby facilitating the flow of the vapor into the airflow channel 11. In some embodiments, the airflow guide structure 40 may be arranged between the vaporization assembly 20 and the air inlet 31, a spacing may be reserved between the airflow guide structure 40 and the vaporization assembly 20, the spacing may form a communication channel 14, and the communication channel 14 is configured to communicate the vaporization cavity 12 with the airflow channel 11.

Further, in some embodiments, the airflow guide structure 40 may include an airflow guide surface 41, and the airflow guide surface 41 is an inclined surface. The airflow guide surface 41 may be arranged opposite to the air inlet 31 and may be arranged towards the closed region 121. The airflow guide surface 41 may be configured to guide a part of the airflow to the closed region 121 of the vaporization cavity 12, and to squeeze, accelerate, and guide the airflow outputted to the airflow channel 11 from the vaporization cavity 12. Further, in some embodiments, a set angle α may be formed between the airflow guide surface and an air inlet end surface of the air inlet 31. In some embodiments, the set angle may be an acute angle. Specifically, in some embodiments, the set angle may be selected as an angle of 30 to 60 degrees.

Further, in some embodiments, the airflow guide structure 40 may further include an overflow surface 42, and the overflow surface 42 may be arranged opposite to the vaporization surface 21. In some embodiments, the overflow surface 42 may be a flat surface, an angle may be formed between the overflow surface 42 and the airflow guide surface 41, and the angle may be equal to the set angle α. Certainly, it may be understood that, in some other embodiments, the overflow surface 42 may not be limited to a flat surface. A spacing between the overflow surface 42 and the vaporization surface 21 may form the communication channel 14. In some embodiments, the distance between the overflow surface 42 and the vaporization surface 21 may be greater than zero and not greater than ⅔ of the height of the vaporization cavity 12. Specifically, in some embodiments, the distance between the overflow surface 42 and the vaporization surface may be ⅓ to ⅔ of the height of the vaporization cavity.

Further, in some embodiments, two opposite sides of the airflow guide structure 40 may respectively extend to the side wall of the housing 10 along the width direction of the housing 10, and may be connected to the side wall 10. In some embodiments, the airflow guide structure 40 and the housing 10 may be integrally formed. Specifically, in some embodiments, the airflow guide structure 40 and the housing 10 may be integrally formed through injection.

The airflow inside the vaporization cavity 12 of the electronic vaporization device of the present invention is better, the overall performance is improved, and the e-liquid lead-out effect is better.

Figure 4:
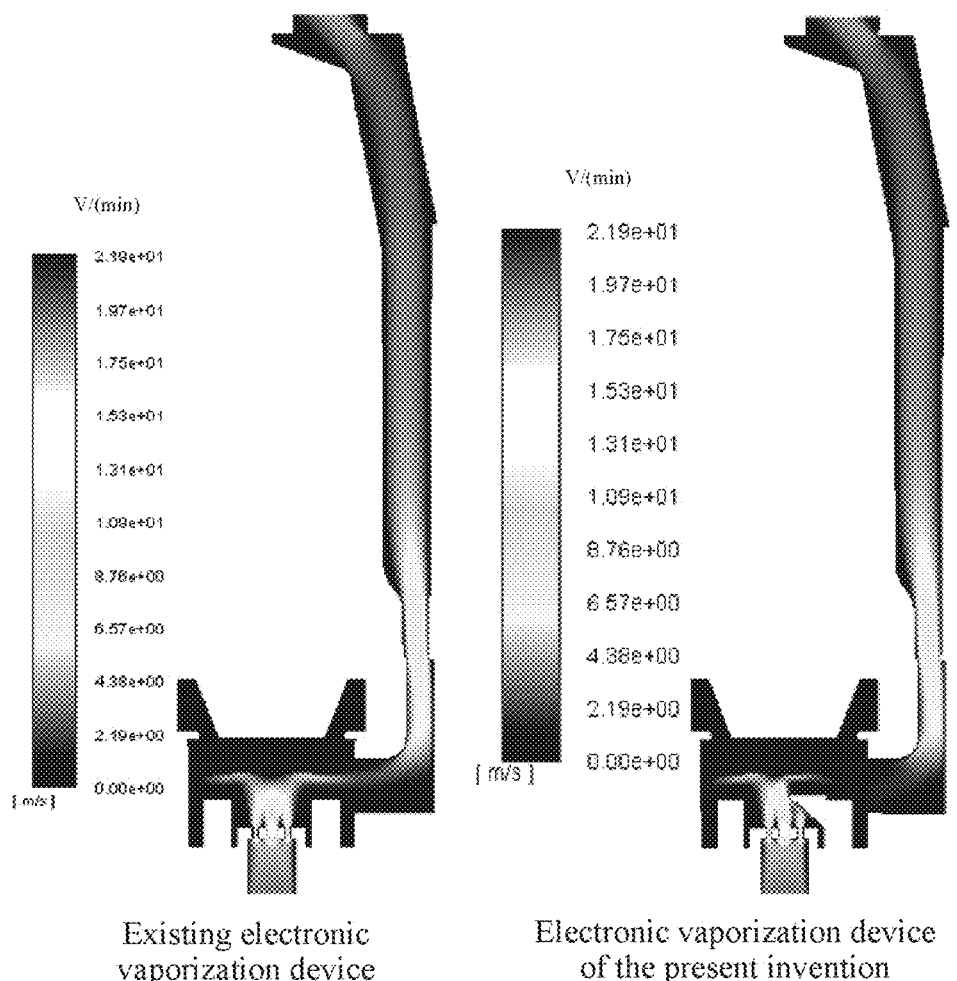
FIG. 4 is a comparison diagram of vapor velocity field between the electronic vaporization device of the present invention and an existing electronic vaporization device.

As shown in FIG. 4, by comparing the velocity field of the vapor of the electronic vaporization device of the present invention with that of the vapor of the existing electronic vaporization device, the velocity field inside the vaporization cavity 12 changes after the airflow guide structure 40 is added, and a part of the airflow from the air inlet 31 can be drained to the closed end 121 of the vaporization cavity 12 through turning of the airflow guide structure 40.

Figure 5:
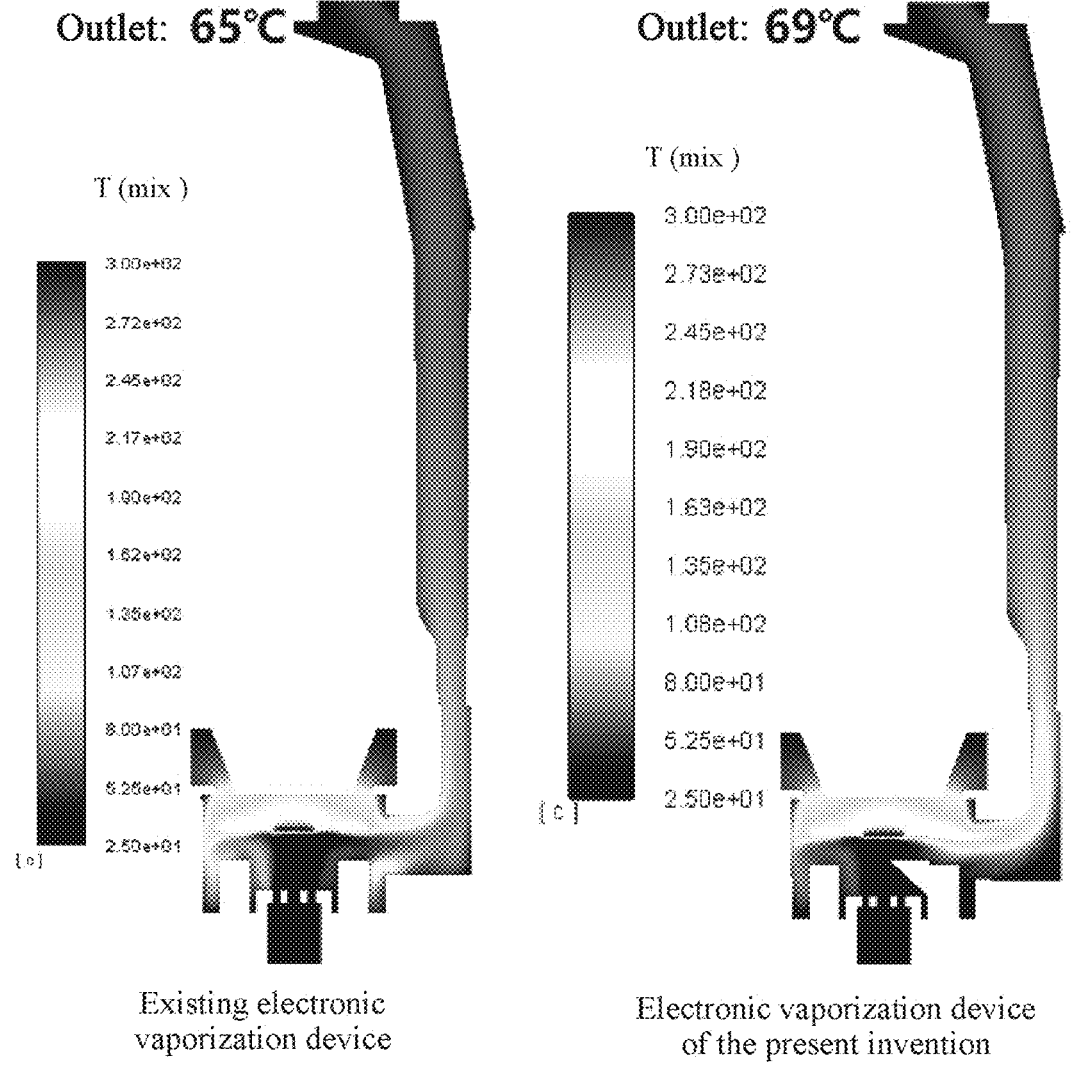
FIG. 5 is a comparison diagram of vapor lead-out temperature between the electronic vaporization device of the present invention and an existing electronic vaporization device.

As shown in FIG. 5, by comparing the lead-out temperature of the vapor of the electronic vaporization device of the present invention with that of the vapor of the existing electronic vaporization device, firstly, the temperature of the vapor sent from the air outlet 15 of the electronic vaporization device of the present invention is 69° C., the outlet temperature of the vapor is increased by 4° C. compared with the existing electronic vaporization device; secondly, the airflow temperature of the closed end 121 of the vaporization cavity 12 of the electronic vaporization device of the present invention is about 20° C. lower than that of the closed end 121 of the existing electronic vaporization device, the high-temperature region of the closed end 121 is also reduced; and moreover, after the airflow guide structure 40 is added, the heat transfer intensity between the airflow and the vaporization surface 21 increases, and the temperature distribution in the turning section is greatly improved compared with the existing electronic vaporization device.

Figure 6:
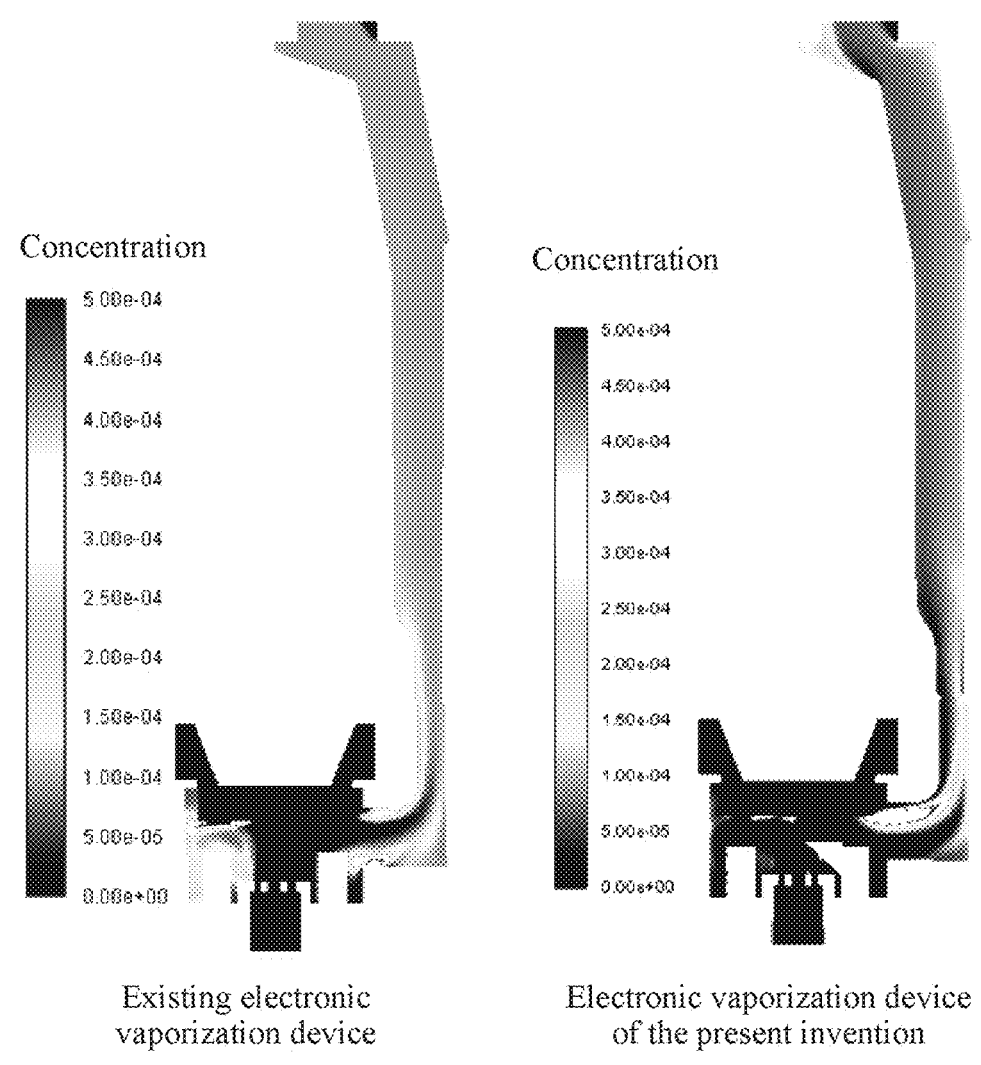
FIG. 6 is a comparison diagram of e-liquid concentration field in a vaporization cavity of an electronic vaporization device of the present invention and an existing electronic vaporization device.

As shown in FIG. 6, by comparing the e-liquid concentration field in the vaporization cavity of the electronic vaporization device of the present invention with that of the vaporization cavity of the existing electronic vaporization device, the e-liquid accumulation inside the vaporization cavity 12 of the electronic vaporization device of the present invention is reduced, this is because after the airflow guide structure 40 is added, the airflow inside the vaporization cavity 12 changes from being disordered to being regular, and generation of eddy current inside the vaporization cavity 12 is reduced. In the vaporization cavity 12 of the electronic vaporization device of the present invention, the amount of carried e-liquid of the turning section is significantly increased, and the shape of "downward warping" is presented, so that the contact with the wall surface of the turning section is reduced.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A vaporizer, comprising:

a housing; and a vaporization assembly arranged in the housing, a vaporization cavity configured to accommodate the vaporization assembly being arranged in the housing, and an airflow channel being arranged in the housing at one side of the vaporization cavity and in communication with the vaporization cavity;

an air inlet in communication with the vaporization cavity; and an airflow guide structure arranged in the vaporization cavity and configured to guide an airflow at the air inlet, wherein the airflow guide structure is arranged close to the airflow channel, wherein the airflow guide structure is arranged between the vaporization assembly and the air inlet, wherein a spacing is reserved between the airflow guide structure and the vaporization assembly, wherein the spacing forms a communication channel that communicates the vaporization cavity with the airflow channel, wherein the vaporization cavity further comprises a closed region arranged opposite the airflow channel, wherein the airflow guide comprises an airflow guide surface obliquely angled relative to an air inlet end surface of the air inlet, and wherein the airflow guide surface is arranged towards the closed region so as to guide a part of the airflow to the closed region of the vaporization cavity, and squeeze, accelerate, and guide the airflow outputted to the airflow channel from the vaporization cavity.

2. The vaporizer of claim 1, wherein the airflow guide surface forms an acute angle relative to the air inlet end surface.

3. The vaporizer of claim 1, wherein the air inlet comprises a central axis, and wherein the airflow guide structure is arranged only at one side of the central axis.

4. The vaporizer of claim 1, wherein a size of the airflow guide structure is smaller than a size of the vaporization cavity.

5. The vaporizer of claim 1, wherein the vaporization assembly comprises a vaporization surface arranged opposite the vaporization cavity, wherein the airflow guide structure comprises an overflow surface arranged opposite the vaporization surface, and wherein the communication channel is arranged between the overflow surface and the vaporization surface.

6. The vaporizer of claim 5, wherein a distance between the overflow surface and the vaporization surface is greater than zero and not greater than ⅔ of a height of the vaporization cavity.

7. The vaporizer of claim 1, wherein a cross section of the housing comprises a length direction and a width direction, and wherein two opposite sides of the airflow guide structure respectively extend to a side wall of the housing along the width direction of the housing.

8. The vaporizer of claim 1, wherein the airflow guide structure and the housing are integrally formed.

9. The vaporizer of claim 1, wherein the airflow guide structure is in a shape of a triangle, a wedge, or a trapezoid.

10. The vaporizer of claim 1, further comprising:

two electrode columns conductively connected to the vaporization assembly, wherein the two electrode columns are spaced apart, and wherein the airflow guide structure is arranged entirely between the two electrode columns.

11. The vaporizer of claim 1, further comprising:

a base, wherein the housing is sleeved on the base, and wherein the air inlet is arranged on the base.

12. An electronic vaporization device, comprising:

the vaporizer of claim 1; and a power supply assembly connected to the vaporizer.

* * * * *